US008557589B2

(12) United States Patent \
Eccleston et al.

(10) Patent No.: US 8,557,589 B2 \
(45) Date of Patent: Oct. 15, 2013

(54) METHOD FOR QUANTITATIVELY DETERMINING THE DYE CONTENT IN DYED OILS

(75) Inventors: Holly S. Eccleston, Salem, CT (US); Mimi Nguyen-Vu, Newington, CT (US); Philip H. Ratliff, Cheshire, CT (US)

(73) Assignee: United Technologies Corporation, Hartford, CT (US)

( * ) Notice: Subject to any disclaimer, the term of this patent is extended or adjusted under 35 U.S.C. 154(b) by 850 days.

(21) Appl. No.: 12/387,102

(22) Filed: Apr. 28, 2009

(65) Prior Publication Data

US 2010/0113311 A1    May 6, 2010

Related U.S. Application Data

(62) Division of application No. 11/647,099, filed on Dec. 28, 2006, now abandoned.

(51) Int. Cl. \
 *G01N 31/00*    (2006.01)

(52) U.S. Cl. \
 USPC .............................................. 436/60; 73/40.7

(58) Field of Classification Search \
 None \
 See application file for complete search history.

(56) References Cited

U.S. PATENT DOCUMENTS

| | | | |
|---|---|---|---|
| 5,304,493 A | 4/1994 | Nowak | |
| 5,919,707 A | 7/1999 | Banks | |
| 5,979,226 A | 11/1999 | Cavestri | |
| 6,002,056 A * | 12/1999 | Smith et al. | 585/3 |
| 6,132,636 A | 10/2000 | Singh | |

FOREIGN PATENT DOCUMENTS

| | | |
|---|---|---|
| EP | 0543057 A | 5/1993 |
| JP | 2006526771 | 11/2006 |

OTHER PUBLICATIONS

Weissler P: "Saturday Mechanic: Finding Oil Leaks" Popular Mechanics, [Online], Jul. 1, 2002, XP007911183, Retrieved from Internet: URL: http://www.popularmechanics.com/how_to_central/automotive/1272471.html?do=print> [retrieved on Jan. 18, 2010]. \
Extended Search Report mailed on Jan. 27, 2010 for EP07255024. \
"Standard addition", Wikipedia, Nov. 7, 2006, pp. 1-2, XP55026910, Retrieved from the Internet: URL:http://en.wikipedia.org/w/index. php?title=Special:Book&bookcmd=download&collection_id=. \
"Chapter 11: Spectrophotometer", Male declaration: Technical Manual: Manual for national training programme, Jul. 2, 2004, pp. 65-72, XP55026912, Retrieved from the Internet: URL:http://www.rrcap.unep.org/male/manual/national/.

* cited by examiner

*Primary Examiner* — Robert Xu \
(74) *Attorney, Agent, or Firm* — Carlson, Gaskey & Olds, P.C.

(57) ABSTRACT

A new method to determine by quantitative analysis the amount of dye present in dyed engine oils is provided. The method uses imaging techniques, such as spectrophotometry, and a combination of dilution and standard addition techniques to quantitatively determine the concentration of dye in the engine oil to ascertain whether dye concentrations in engine oil have decreased as compared with original specifications, and to quantify the amount of dye to be added to the dyed engine oil to bring dye concentrations to original concentrations.

25 Claims, 2 Drawing Sheets

| THRESHOLD: | 0.050 | | |
|---|---|---|---|
| SAMPLE | CYCLE | WAVELENGTH | DATA |
| 009 | 01:26 | 654.8 nm (MAX) | 0.810 ABS |
| | | 628.5 nm (MIN) | 0.555 ABS |
| | | 606.9 nm (MAX) | 0.744 ABS |

METHOD FOR QUANTITATIVELY DETERMINING THE DYE CONTENT IN DYED OILS

This disclosure is a Divisional of U.S. patent application Ser. No. 11/647,099, filed Dec. 28, 2006, now abandoned.

BACKGROUND OF THE INVENTION

1. Field of Invention

The present disclosure is generally related to oil such as engine and/or lubricant oil and, in particular, the analysis and use of dyed oils.

2. Description of the Related Art

Determination of the origin of oil leaks for engines, turbines and the like, can be a difficult problem whether the equipment is being newly-built, tested, repaired or rebuilt. The problem is exacerbated by the presence of build oil or assembly oil that is already on the outer Surface of the engine, so that it may be difficult to determine the source of the oil. The problem of phantom oil leaks, in particular, often results in unnecessary engine teardowns.

One remedy to the problem has been to add dye into engine oil during engine testing, so that detection of the dyed oil on the outside of the engine would indicate the presence of an oil leak. However, while this method may show, qualitatively, whether or not there is a leak, there are problems with this method. One problem with visual detection is that the dye is often mixed with oils of various brands and ages. These oils have colors varying from pale yellow to black brown (depending on the composition of the oil and the effects of age and wear), making the presence of a small amount of dye on the surface of the engine difficult to ascertain. This problem is exacerbated by the presence of assembly oil on the surface of the engine which may further dilute or shield the dye from observation. Visual methods to detect the dye are not effective due to darkening of oil with age and use.

Accordingly, there is a need for a method for determining the amount of dye present in dyed engine oils. There is a further need for such a method that can be utilized in distinguishing the origin of oil observed on the outer surface of an engine as being from engine oil or build oil. There is a further need for quantifying the amount of dye needed to be added to engine oil to bring the dye concentration back into the specified concentration range so that the oil may be used for subsequent engine testing.

SUMMARY OF THE INVENTION

The method disclosed herein determines, by quantitative analysis, the amount of dye present in dyed engine oil. The quantitative analysis uses imaging methods, such as UV-Vis spectrophotometry, to measure the absorbance values of the dye in a spiked test sample drawn from the engine oil, and compares the absorbance values of the spiked test sample with absorbance values measured for two or more standard solutions of dyed engine oil and dye that are prepared by standard addition techniques. The concentration of the dye in the test sample is then determined using an algorithm, mathematical model or other such analysis, such as, for example, linear regression analysis, and the amount of dye currently present in the engine oil is calculated. This data may be used to calculate the precise amount of dye required to bring the dye concentration in the engine oil back into the specified concentration range. Any required addition of dye would then be made to the engine oil, which could then be used in a subsequent engine test. The present disclosure refers generally to engines that use oil but it should be understood by one of ordinary skill in the art that the term is a non-limiting example of a device, system and/or equipment that utilizes oil and/or lubricant, and for which the present disclosure is applicable. The present disclosure refers generally to engine oil that is dyed but it should be understood by one of ordinary skill in the art that the term is a non-limiting example of a type of oil or lubricant for which the present disclosure is applicable.

The method disclosed herein offers several advantages over the previous methods. The method disclosed more readily detects dyed engine oil even where the background color of the engine oil makes visual detection or instrumental detection of a dye difficult or impossible. The method can be used effectively where dyed engine oil is used, whether the engine is being newly-built, tested, repaired, or rebuilt. In addition, the method provides a means to calculate the exact amount of dye that must be added to the engine oil to replace the amount of dye lost because of dilution where oil is added from another source. The method disclosed herein is advantageous due to its quantitative analysis of the dyed engine oil.

DETAILED DESCRIPTION OF THE INVENTION

Figure 1:
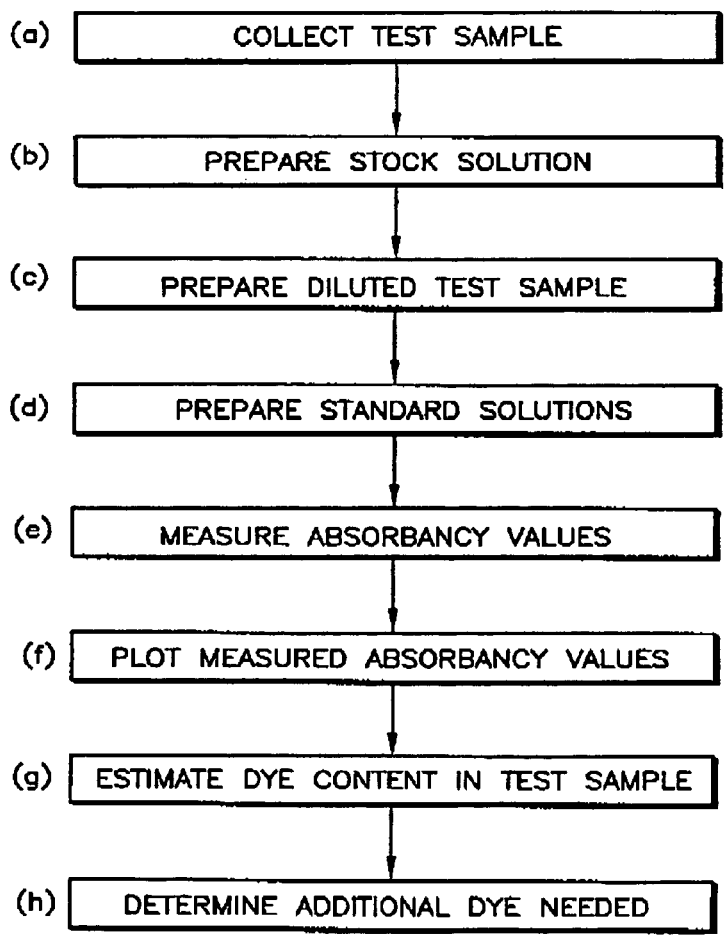
FIG. 1 is a flow chart of the method to determine, by quantitative analysis, the amount of dye present in engine oil.

The present disclosure provides a method to quantitatively analyze the amount of dye present in engine oil. The dyed engine oil reduces unnecessary engine teardowns due to phantom oil leaks. In addition, the method provides a means to calculate the amount of dye to be added to the recycled oil to bring the dye concentration in engine oil back into the specified concentration range. The method is also used as a quality control method for maintaining the required concentration of dye in the engine oil.

The method disclosed herein includes, but is not limited to, the following: (a) collecting a test sample of engine oil to which a dye had been previously added; (b) preparing a stock solution of the dyed engine oil by taking a known amount (weight) of dye and diluting it approximately 100-fold with a known weight of new engine oil, and calculating the concentration of the stock solution by the equation (where the symbol "*" indicates multiplication):

[concentration of stock solution, parts per million (ppm)]=(mass of dye, grams (g)÷mass of new engine oil, g)*$10^6$ ppm;

(c) preparing a diluted test sample by diluting the test sample between eight-fold and twelve-fold with a non-reactive solvent; (d) preparing two or more standard solutions of dyed engine oil, wherein the two or more standard solutions contain incrementally-increasing weights of the stock solution (such as 0.02 grams, 0.04 grams, 0.06 grams, etc.) which are then diluted to the same final weight by addition of the diluted test sample, and the actual concentration of each standard solution may be calculated by the equation:

(mass of stock solution, g*[concentration of stock solution, ppm])÷mass of diluted test sample, g;

(e) measuring by spectrophotometry the absorbance values of the dye in the diluted test sample and the two or more standard solutions at a pre-selected peak wavelength corresponding specifically to the dye used; (f) plotting the maximum measured absorbance values of the standard solutions versus concentrations of dye added to the standard solutions and plotting or calculating the equation of a best-fit line through the data points corresponding to the two or more standard solutions by linear regression analysis, where the best-fit line is expressed as an equation of the form y=mx+b, where x is the concentration of the dye in the standard solution, y is the absorbance value, m is the slope of the line, and b is the y-axis intercept corresponding to a standard solution with zero dye added; (g) determining the concentration of the dye in the original test sample by plotting the absorbance value of the diluted test sample on the best-fit line; or, alternatively, by calculating the concentration by the slope m of the intercept b, where y=mx+b is the equation of the best-fit line and the concentration of dye in the engine oil is:

$b \div m *$ dilution factor; and (h) determining by calculation an amount of dye to be added back into the engine oil to bring the concentration of dye within original specifications, using the following formulae:

$A$=amount of dye to be added=starting concentration of dye (approximately 150 ppm)−present calculated concentration of dye;

$B$=mass of 1 gallon of oil=3766 grams;

$C$=mass of dye to add (grams)=$B$ times $A$ divided by $10^6$ (parts per million); and $D$=amount of dye in milliliters (mL) to add per gallon of oil=$C \div 0.96$ (g/mL).

A flow chart diagram of the method is provided in FIG. 1. While the steps of this method are disclosed above in a particular order, the present disclosure contemplates that the steps can be conducted in a different order to quantitatively analyze the amount of dye present in engine oil.

The dyed oil discriminates between actual oil leaks and non-existent or phantom oil leaks, thereby significantly reducing the need for unnecessary engine teardowns attributable to phantom oil leaks.

The present disclosure utilizes a specific combination of dilution and standard addition techniques to accurately determine the quantity of dye present in engine oil. The method provides test samples that are suitable for measurement by spectrophotometry even where the background color of the engine oil would shield or otherwise interfere with measurement of the absorption of light by the dye.

The combination of dilution and standard addition techniques in the method also overcomes the problem of background interference due to the use of various grades of oils and mixtures of new, used, and/or recycled oils when conducting spectrophotometric analysis of the diluted test sample and standard solutions described below.

The method involves collection and quantitative analysis of engine oil to which an amount of dye has been previously added (FIG. 1). For this particular UV-Vis spectrophotometric analysis, the dye may be any dye with a peak absorbance wavelength in the UV-Visible range. The UV-Visible range is defined as wavelengths of approximately 400 nm to 700 nm. For example, the dye used in the method may be a blue dye, red dye, bronze dye, orange dye or green dye. However, the method can be utilized with, and adapted for, various dyes or other inspection additives. Blue Dye is the only dye currently approved for use under the United States Department of Defense Performance Specification MIL-PRF-23699 (Gas Turbine Lubricating Oils). An example of a blue dye that is useful for this method is commercially available OCTEL-STARREON OIL BLUE B LIQUID DYE™ (Octel-Starreon, LLC, Littleton, Colo., USA). The specified concentration of blue, dye to be used in this method is about 150 parts per million (ppm) with the acceptable range from about 110 ppm to 190 ppm.

Figure 2:
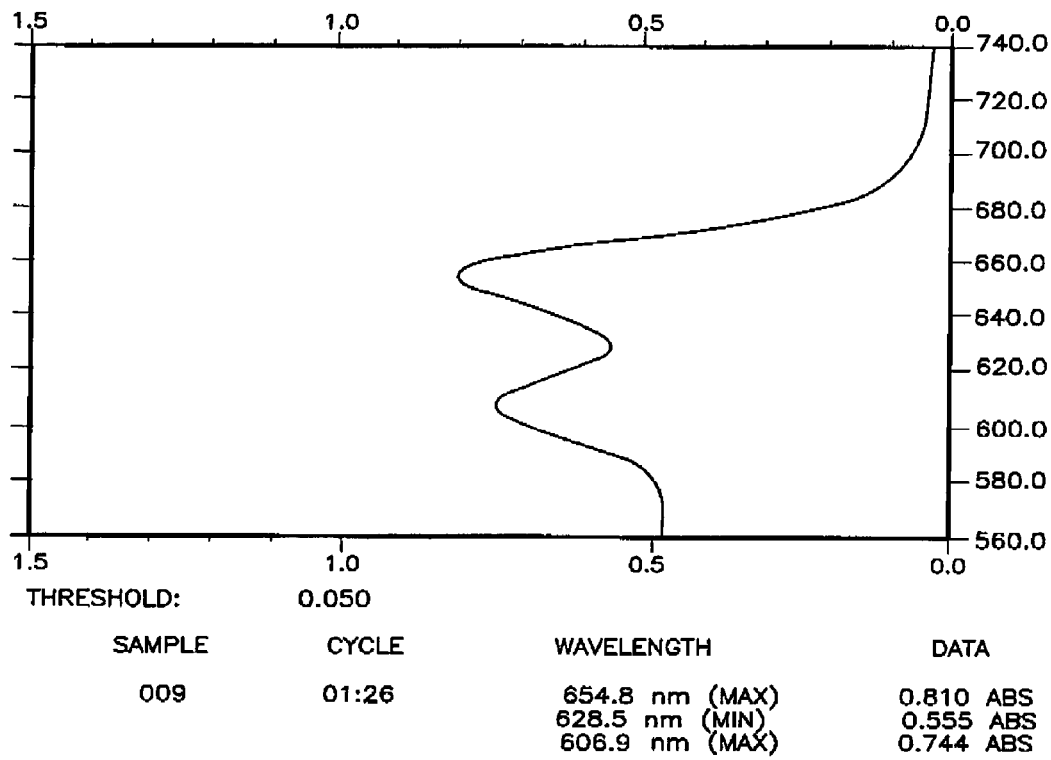
FIG. 2 is a typical UV-Vis spectrophotometric scan of absorbance values of a solution of blue dye in engine oil showing a peak absorbance value for blue dye at about 655 nanometers.

When analyzed by spectrophotometry, each color or type of dye will have a wavelength at which it shows the strongest absorbance signal. The wavelength at which this occurs is termed, for purposes of the quantitative analysis, the pre-selected peak wavelength. One method to determine the pre-selected peak wavelength for a particular color of dye is to expose a sample of the dye to a UV-Vis spectrophotometric scan running between wavelengths of 400 nm to 700 nm, with a threshold limit of 0.05 and a scan rate of 240 nm/minute, generating the typical graph of a UV-Vis scan such as is shown in FIG. 2. The strongest absorbance value, or peak, corresponds to that wavelength which is then identified as the pre-selected peak wavelength for that particular dye. For example, the commercially-available hydrocarbon-soluble blue dye OCTEL-STARREON OIL BLUE B LIQUID DYE™ has a peak absorbance value at a wavelength of about 655 nanometers (nm) when measured by Ultraviolet-Visible (UV-Vis) spectrophotometry, as shown also by FIG. 2. Each color and type of dye will have its own specific corresponding peak absorbance values at a particular wavelength when measured by UV-Vis spectrophotometry, which is then identified as the pre-selected peak wavelength.

The method disclosed herein may be used with engine oils of various grades, including new oil, used oil, mixed oils, and recycled oils. The method is also applicable to any lubricating oil including, but not limited to, those lubricating oils that meet the Mil-PRF-23699F Specification (effective May 21, 1997) published by the U.S. Department of Defense, which includes three classes of gas turbine engine lubricating oils, primarily used for aircraft engines, which have a nominal viscosity of 5 centistokes at 100° C. and which are typically made with neopentyl polyol ester base stocks. Examples of such oils include EXXON/MOBIL JET OIL II™ and MOBIL 254™ (Mobil Oil Corporation, Fairfax, Va., USA), BP TURBO OIL 2197™ and BP TURBO OIL 2983™ (Air BP Lubricants, Parsippany, N.J., USA).

The method disclosed herein may be used for any type of gas turbine engine including industrial and aircraft gas turbine engines, as well as other types of oil/lubricant required devices and/or systems.

The stock solution used in the quantitative analysis is prepared by diluting a known amount of dye in a solution of new engine oils to a concentration of about 10,000 ppm (FIG. 1, (b)), with an acceptable concentration range from about 8,000 ppm to about 12,000 ppm. The actual concentration is determined using the following equation below:

concentration of Stock Solution (ppm) equals the mass of dye (grams) divided by mass of oil (grams), multiplied times $10^6$.

Preferred new engine oils useful for creating the stock solutions used in this method are synthetic turbine lubricating oils, such as the commercially-available products EXXON/MOBIL JET OIL II™ (Mobil Oil Corporation, Fairfax, Va., USA) and BP TURBO OIL 2197™ (Air BP Lubricants, Parsippany, N.J., USA).

The two or more standard solutions which are analyzed by UV-Visible spectrophotometry to create the best-fit line are prepared by adding incrementally-increasing amounts of the stock solution described above (0.02 grams, 0.04 grams, 0.06 grams, etc.), and diluting each with a portion of the diluted test sample solution to a total mass of 10 grams (FIG. 1, (d)). The resulting standard solutions are designated the "0.02," "0.04," 0.06," etc. standard solutions, respectively. One of the standard solutions containing a portion of the diluted test sample without adding any stock solution is designated the "0.00" standard solution.

Incrementally-increasing amounts are defined as the series of amounts of the stock solution which are added to the test sample and are associated in a linear fashion when graphed so as to be useful for standard addition, such as 0.02 grams, 0.04 grams, 0.06 grams, 0.08 grams, etc.

In this method, the standard solutions of dye in engine oil used to plot the best-fit line by linear regression are themselves prepared by the technique of standard addition. Preferably, a minimum of three absorbance values are used to accurately develop the best-fit line by linear regression analysis. This may be accomplished by preparing three or more standard solutions by adding dye in the amounts of 0.02 grams, 0.04 grams, and 0.06 grams, respectively, to a portion of the diluted test sample drawn from the dyed engine oil. However, in the event that the stock solution labeled "0.00" (i.e., zero grams of added dye) has a strong absorbance signal (e.g., >0.2 ABS or Absorbance) at the pre-selected peak wavelength, then only two additional standard solutions need to be prepared, and the standard solutions adding 0.06 grams of dye or greater may be eliminated to save time and resources.

The actual concentrations of each of the "0.02," "0.04," and "0.06" standard solutions are calculated by the following equation:

concentration (ppm) equals the mass of stock solution (grams) multiplied times the Concentration of stock solution (ppm), divided by the Mass of the diluted test sample (grams).

For example, if the commercially-available blue dye OCTEL-STARREON OIL BLUE B LIQUID DYE™ is used for this method, the 0.06 standard solution may be eliminated to save time and resources if the 0.00 standard solution (i.e., the stock solution to which zero additional dye has been added) has an absorbance value of at least 0.2 ABS at about 655 nanometers (nm) when measured by UV-Vis spectrophotometry.

After the test sample is collected from engine oil (FIG. 1, (a)), a "diluted test sample" is prepared by diluting the test sample in a non-reactive solvent in a ratio that varies preferably from eight-fold to twelve-fold, with best results using a ten-fold dilution. (FIG. 1, (c)). As an example, the diluted test sample may be prepared by weighing 5.0 grams of the test sample and diluting the test sample with the non-reactive solvent to 50 grams of total weight. The dilution factor for the test sample is calculated by the following equation:

dilution factor of test sample equals Total Mass of diluted test sample (grams) divided by mass of original test sample (grams).

The dilution step imparts at least two advantages to the method: dilution thins the engine oil in the test sample to reduce background interference with measurement of absorbance values by spectrophotometry; and dilutes the dye to bring the strength of the absorbance signals of the dye closer to the range of absorbance signals generated by the two or more standard solutions making up the best-fit line, reducing the variability. Another benefit is that the two or more standard solutions that are prepared for this method use smaller amounts of added dye to generate the data for best-fit line. By comparison, two-fold (1:2) dilution of the test sample generally yields samples that are too dark, or opaque because of the background oil and the dye to permit useful measurements of absorbance by spectrophotometry. Conversely, dilutions of fifteen-fold (1:15) or twenty-fold (1:20) or higher cause the signal from the dye to be too weak for the quantitative analysis of this method. However, the present disclosure contemplates the use of other dilution ratios, especially where such other ratios reduce background interference and/or increase accuracy of the particular analysis method being utilized, such as UV-Vis spectrophotometry described herein.

The non-reactive solvent used to dilute the test sample in this method is preferably acetone for most ester-based synthetic oils, or may be selected from other non-reactive solvents of similar polarity to acetone. For 10/10 grade oil, the preferred non-reactive solvent is hexanes. Other oil/solvent combinations may be used, preferably such oil/solvent combinations which have similar polarities to each other.

The diluted test sample may then be analyzed by spectrophotometry at the pre-selected peak wavelength (corresponding to the dye used) to measure an absorbance value for the test sample (FIG. 1, (e)).

A minimum of three data points showing absorbance values at the pre-selected peak wavelength for three standard solutions are used to create an acceptable best-fit line by linear regression for purposes of the quantitative analysis.

Preparing additional standard solutions by the standard addition technique described above (such as adding 0.01 grams, 0.03 grams, 0.05 grams, etc.) will improve the accuracy of the line formed by linear regression analysis, but are generally not necessary for the method to be effective. Absorbance values should preferably be held below 2.0 to avoid saturating the detector.

As an example of the method, the four standard solutions labeled 0.00, 0.02, 0.04, and 0.06 are analyzed by UV-Vis spectrophotometry by first performing a background correction by placing the non-reactive solvent (such as acetone) in each of the UV cells and analyzing each for background correction. For accuracy of the spectrophotometric measurement, good-quality matched cells should be used, and fingerprints should be avoided on the windows of the cells. The cells should be rinsed between analyses by triple-rinsing the cell windows with the solution to be analyzed. The UV-Vis spectrophotometer should be set to scan from 560 nm to 740 nm, with a threshold limit of 0.05 and a scan rate of 240 nm/minute.

The absorbance values of the four standard solutions (labelled 0.00, 0.02, 0.04, and 0.06) are then measured at the pre-selected peak wavelength (FIG. 1, (e)), and the results are plotted on a graph (FIG. 1, (f)). Where the dye used in the quantitative method is the blue dye OCTEL-STARREON OIL BLUE B LIQUID DYE™, the absorbance values of the four standard solutions at about the pre-selected peak wavelength of 655 nm should be plotted on a graph of Absorbance versus Concentration of Dye Added. Background correction for the non-reactive solvent (see above) should be incorporated.

Figure 3:
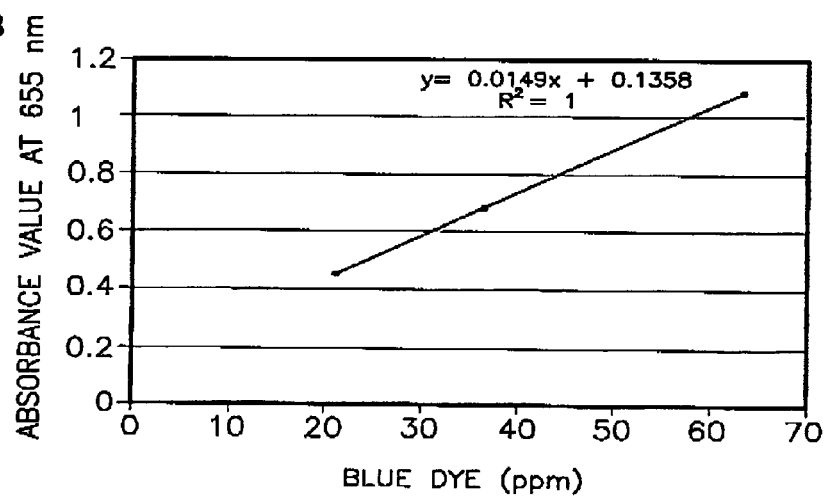
FIG. 3 is a typical best-fit line of the form y=mx+b created by linear regression techniques using three points from the standard solutions created by standard addition.

A best-fit line for these data points is created using linear regression techniques (FIG. 1, (f)), and, for greater accuracy, a mathematical equation for the best-fit line of the form y=mx+b should be calculated. FIG. 3 provides an example of a best-fit line generated by linear regression.

The concentration of dye in the test sample is then calculated from the slope m of the intercept b, where the best-fit line is represented by the equation y=mx+b (FIG. 1, (g)). The concentration of the dye in the engine oil is calculated by the following equation:

[concentration of dye]=b÷m*dilution factor

The method also provides a means to determine the amount of dye to be added to the engine oil per one gallon of the engine oil to bring the dye concentration within original specifications, which means a dye concentration at about 150 ppm (±40 ppm) for purposes of this exemplary method. The amount and volume of dye needed for this purpose is calculated as follows (FIG. 1, (h)):

$A$=amount of dye to be added=starting concentration of dye (approximately 150 ppm)−present calculated concentration of dye;

$B$=mass of 1 gallon of oil=3766 grams;

$C$=mass of dye to add (grams)=$B$ times $A$ divided by $10^6$ (parts per million); and $D$=amount of dye in milliliters (mL) to add per gallon of oil=$C$÷0.96 (g/mL). (Note—0.96 g/mL=density of the oil)

Any required addition of dye would then be made to the engine oil to bring the concentration of dye back within specified limits, to be used again in a subsequent engine test.

EXAMPLE 1

OCTEL-STARREON OIL BLUE B LIQUID DYE™ (Octel Starreon, LLC, Littleton, Colo., USA) is added to engine oil at a concentration of about 150 ppm (±40 ppm) to facilitate detection of oil leaks. The engine oil is a combination of new, used, mixed, and recycled oils.

A test sample of the dyed engine oil is collected for analysis. The test sample is then diluted ten-fold in acetone to create a diluted test sample.

Separately, about 1 gram of OCTEL-STARREON OIL BLUE B LIQUID DYE™ is added to about 100 grams new EXXON/MOBIL JET OIL II™ (Mobil Oil Corporation, Fairfax, Va.) to create a stock solution having a dye concentration of approximately 10,000 ppm to be used for the preparation of the two or more standard solutions by standard addition.

Three standard solutions are prepared by weighing 0.02 grams, 0.04 grams, and 0.06 grams of the stock solution and diluting each to 10 grams with the diluted test sample to create three standard solutions (designated "0.02," "0.04," and "0.06," respectively). A fourth standard solution is made from 10 grams of the diluted test sample without adding any of the stock solution, which was designated "0.00 ppm." The actual concentration of dye in the standard solution to which 0.02 grams of stock solution added is 21.15 ppm. The concentration of the standard solution to which 0.04 grams of the stock solution was added is calculated to be 36.48 ppm. The concentration of the standard solution to which 0.06 grams of the stock solution was added is calculated to be 63.41 ppm. These three standard solutions are measured for absorbance values at the pre-selected peak wavelength of 655 nm (corresponding to this particular blue dye) by UV-Vis spectrophotometry:

| Blue Dye (grams of stock solution) | Blue Dye (ppm) | Absorbance value |
| --- | --- | --- |
| 0.02 | 21.15 | 0.451 |
| 0.04 | 36.48 | 0.680 |
| 0.06 | 63.41 | 1.08 |

Note:
Because the 0.00 ppm standard solution has no peaks detected, the 0.06 standard solution is needed to provide a third data point to generate a best-fit line.

The absorbance values of the standard solutions (0.02, 0.04, and 0.06) are plotted on a graph and a best-fit line of form y=mx+b is generated by linear regression techniques.

The best-fit line using data from Example 1 is shown in FIG. 3. The best-fit line has the equation y=0.0149 x+0.1358. Using this equation and the absorbance value of the diluted test sample, the current concentration of blue dye in the test sample is calculated to be 90.2 ppm.

The amount of blue dye to add back into the engine oil, as calculated using the equations provided above, is found to be 0.23 mL of blue dye per gallon of oil. The method described herein employs UV-Vis spectrophotometry to analyze the standard solutions created for the dyed engine oil. However, the present disclosure contemplates application of the above method with the use of other imaging, chemical imaging and/or spectrophotometry to analyze the standard solutions created for the dyed engine oil.

The method described herein utilizes linear regression analysis to determine the concentrations of dye in the engine oil based upon the data obtained by UV-Vis spectrophotometry on the standard solutions. However, the present disclosure contemplates the use of other data analysis techniques, models and/or algorithms for determining the concentration of dye or other additive which facilitates the method based upon the particular oil, additive, and/or imaging that is being utilized.

The method described herein utilizes standard addition to create standard solutions which are measured for absorbance to provide data for the best-fit curve that is then analyzed using linear regression to determine the concentration of the dye present in engine oil. However, the present disclosure contemplates the use of other methods to generate data used to create a reference curve or "best-fit" line on which the concentration of the dye in the test sample may be plotted or calculated.

The present disclosure utilizes dyes as a marker or additive for the engine oil and/or lubricant, which allows for determining whether an engine has a leak through distinguishing between engine oil and build oil. However, the present disclosure contemplates the above-described method or parts thereof being used with other types of markers or additives that allows for detection and quantification of the marker or additive.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A method for quantitative analysis of engine oil having an unknown concentration of dye, the method comprising:
   preparing a diluted test sample by diluting a test sample of the engine oil with a non-reactive solvent, and calculating the dilution factor by the formula:

dilution factor of test sample equals Total Mass of diluted test sample (grams) divided by mass of original test sample (grams);

preparing a stock solution by adding a known weight of dye to a known weight of new engine oil;
   preparing two or more standard solutions by adding incrementally-increasing weights of said stock solution to said diluted test sample;

measuring absorbance values of said two or more standard solutions by spectrophotometry;

measuring by spectrophotometry the absorbance values of the diluted test sample;

determining the concentration of the dye in the test sample based upon the measured values of said two or more standard solutions and the concentrations of dye added; and comparing the concentration of dye in the test sample with a desired concentration of dye in the engine oil to quantify the amount of dye to be added to said engine oil to bring the dye concentration to the desired concentration.

2. The method of claim 1, further comprising:
determining if oil on an engine is engine oil or build oil based on said concentration of dye present in the engine oil.

3. The method of claim 1, further comprising:
calculating an equation of the best-fit line of the measured absorbance values plotted for said two or more standard solutions having the form: y=mx+b, where y is the measured absorbance value, x is the concentration any one of the incrementally-increasing weights of dye added to the stock solution, m is the slope of the best-fit line, and b is the y-axis intercept absorbance value at the peak absorbance wavelength; and calculating the concentration of the dye in the test sample by the following formula:

[Concentration of dye]=$b+m$*dilution factor.

4. The method of claim 1, further comprising:
calculating an amount of dye to be added to the engine oil to replace any dye losses of dye such that the concentration of dye present in the dyed engine oil is within original specifications, using the following equations:

$A$=amount of dye to be added=original concentration of dye in dyed engine oil (approximately 150 ppm)−present calculated concentration of dye;

$B$=mass of 1 gallon of oil=3766 grams;

$C$=mass of dye to add (grams)=$B$ times $A$ divided by $10^6$ (parts per million); and $D$=amount of dye in milliliters (mL) to add per gallon of oil=$C$÷0.96 (g/mL), wherein the density of oil is 0.96 g/mL.

5. The method of claim 1, wherein the dye has an absorbance peak in the UV-Visible range.

6. The method of claim 5, wherein the dye is selected from the group consisting of a blue dye, red dye, green dye, bronze dye and orange dye.

7. The method of claim 6, wherein said dye is a blue dye.

8. The method of claim 1, wherein the dye is added to the engine oil to achieve a dye concentration between about 110 parts per million (ppm) and about 190 ppm.

9. The method of claim 8, wherein dye is added to said engine oil to achieve a dye concentration of about 150 ppm.

10. The method of claim 1, wherein the non-reactive solvent used to dilute said test sample has a similar polarity to the engine oil.

11. The method of claim 10, wherein the non-reactive solvent used to dilute the test sample is acetone or hexanes.

12. The method of claim 1, wherein said diluted test sample is prepared by diluting the test sample drawn from said dyed engine oil with a non-reactive solvent by a factor of eight-fold (1:8) to twelve-fold (1:12).

13. The method of claim 12, wherein said diluted test sample is prepared by diluting said test sample with said non-reactive solvent by a factor of ten-fold (1:10).

14. The method of claim 1, wherein said spectrophotometry is Ultraviolet-Visible (UV-Vis) spectrophotometry.

15. The method of claim 1, wherein said stock solution is prepared by diluting a dye in new engine oil to a concentration from about 8,000 ppm to about 12,000 ppm.

16. The method of claim 15, wherein the stock solution has a dye concentration of about 10,000 ppm.

17. The method of claim 1, wherein the new engine oil is a synthetic turbine lubricating oil.

18. The method of claim 1, wherein said two or more standard solutions are prepared by diluting a series of incrementally-increasing weights of said diluted test sample with the stock solution to a total weight of each standard solution of about 10 grams, and wherein the actual concentration of each standard solution is calculated using the following equation:

[Concentration of standard solution (ppm)]=mass of stock solution (grams)*concentration of stock solution (ppm)÷mass of diluted test sample (grams).

19. The method of claim 18, wherein the series of incrementally-increasing weights of the diluted test sample are 0.00 (zero) grams, 0.02 grams, 0.04 grams, and 0.06 grams, or any combination thereof.

20. The method of claim 1, wherein the standard solutions contain a blue dye with a pre-selected peak wavelength of about 655 nanometers.

21. The method of claim 20, wherein said two or more standard solutions have a blue dye concentration from about 0 ppm to about 80 ppm, and wherein the absorbance values for said two or more standard solutions are measured by UV-Vis spectrophotometry at the pre-selected peak wavelength and are used as data points to create a best-fit line by linear regression analysis.

22. The method of claim 1, wherein the engine oil is selected from the group consisting of new oil, used oil, mixed oils and recycled oil.

23. A method to determine dye content of an engine oil having an unknown amount of dye, the method comprising:
preparing a stock solution by taking a known amount of dye and diluting it approximately 100-fold with a known weight of new engine oil, and calculating the concentration of the stock solution by the equation:

[concentration of stock solution, parts per million (ppm)]=(mass of dye, grams (g)÷mass of new engine oil, g)*$10^6$ ppm;

preparing a diluted test sample by diluting a test sample of the engine oil between eight-fold and twelve-fold with a non-reactive solvent of similar polarity to said dyed engine oil, and wherein a dilution factor may be calculated by the equation:

dilution factor of test sample equals Total Mass of diluted test sample (grams) divided by mass of original test sample (grams);

preparing two or more standard solutions of said engine oil, wherein the two or more standard solutions contain incrementally-increasing weights of the stock solution which are then diluted to the same final weight by addition of said diluted test sample, and the actual concentration of each standard solution calculated by the equation:

mass of stock solution (grams)*[concentration of stock solution, ppm]÷mass of diluted test sample, (grams);

measuring by spectrophotometry the absorbance values of each of said two or more standard solutions at the preselected peak wavelength;

plotting the maximum measured absorbance values of said standard solutions versus concentrations of dye added in said standard solutions;

plotting a best-fit line or calculating the equation of a best-fit line by linear regression analysis through the data points corresponding to said two or more standard solutions, wherein the best-fit line is expressed as an equation of the form y=mx+b, where x is said concentration of the dye in the standard solution, y is said absorbance value, m is the slope of said best-fit line, and b is the y-axis intercept corresponding to a standard solution with zero dye added;

calculating the concentration of the dye in said test sample as the slope m of said intercept b, and the concentration of dye in the engine oil is calculated by:

[concentration of dye]=$b \div m$*dilution factor; and calculating a mass and volume of dye to be added to the engine oil to bring the concentration of dye in said dyed engine oil within a desired dye concentrations by the following equations:

$A$=amount of dye to be added=desired concentration of dye in dyed engine oil (approximately 150 ppm)−present calculated concentration of dye;

$B$=mass of 1 gallon of oil=3766 grams;

$C$=mass of dye to add (grams)=$B$ times $A$ divided by $10^6$ (parts per million); and $D$=amount of dye in milliliters (mL) to add per gallon of oil=$C \div 0.96$ (g/mL), wherein the density of the oil is 0.96 g/mL.

24. The method of claim 1, wherein said engine oil is an ester-based oil and the dye is hydrocarbon soluble.

25. The method of claim 1, wherein said engine oil is neopentyl polyol ester base stock and the dye is hydrocarbon soluble.

* * * * *